United States Patent [19]
Dechene et al.

[11] Patent Number: 5,287,061
[45] Date of Patent: Feb. 15, 1994

[54] ON LINE TRIBOELECTRIC PROBE CONTAMINATION DETECTOR

[75] Inventors: Ronald L. Dechene, Boxford; Robert E. Newton, Tewksbury, both of Mass.

[73] Assignee: Auburn International, Inc., Danvers, Mass.

[21] Appl. No.: 885,493

[22] Filed: May 19, 1992

[51] Int. Cl.$^5$ .............................................. G01N 27/60
[52] U.S. Cl. ................................. 324/454; 324/71.1
[58] Field of Search ................. 324/454, 71.1, 71.3

[56] References Cited

U.S. PATENT DOCUMENTS 4,922,205  5/1990  Shimizu et al. ..................... 324/454

*Primary Examiner*—Walter E. Snow
*Attorney, Agent, or Firm*—Jerry Cohen; Edwin H. Paul

[57] ABSTRACT

An improved input circuit (9) for accepting a signal from a triboelectric probe (2). The circuitry provides gain, zero and probe contamination information which allows verification of said information without taking the probe and instrument off-line.

12 Claims, 1 Drawing Sheet

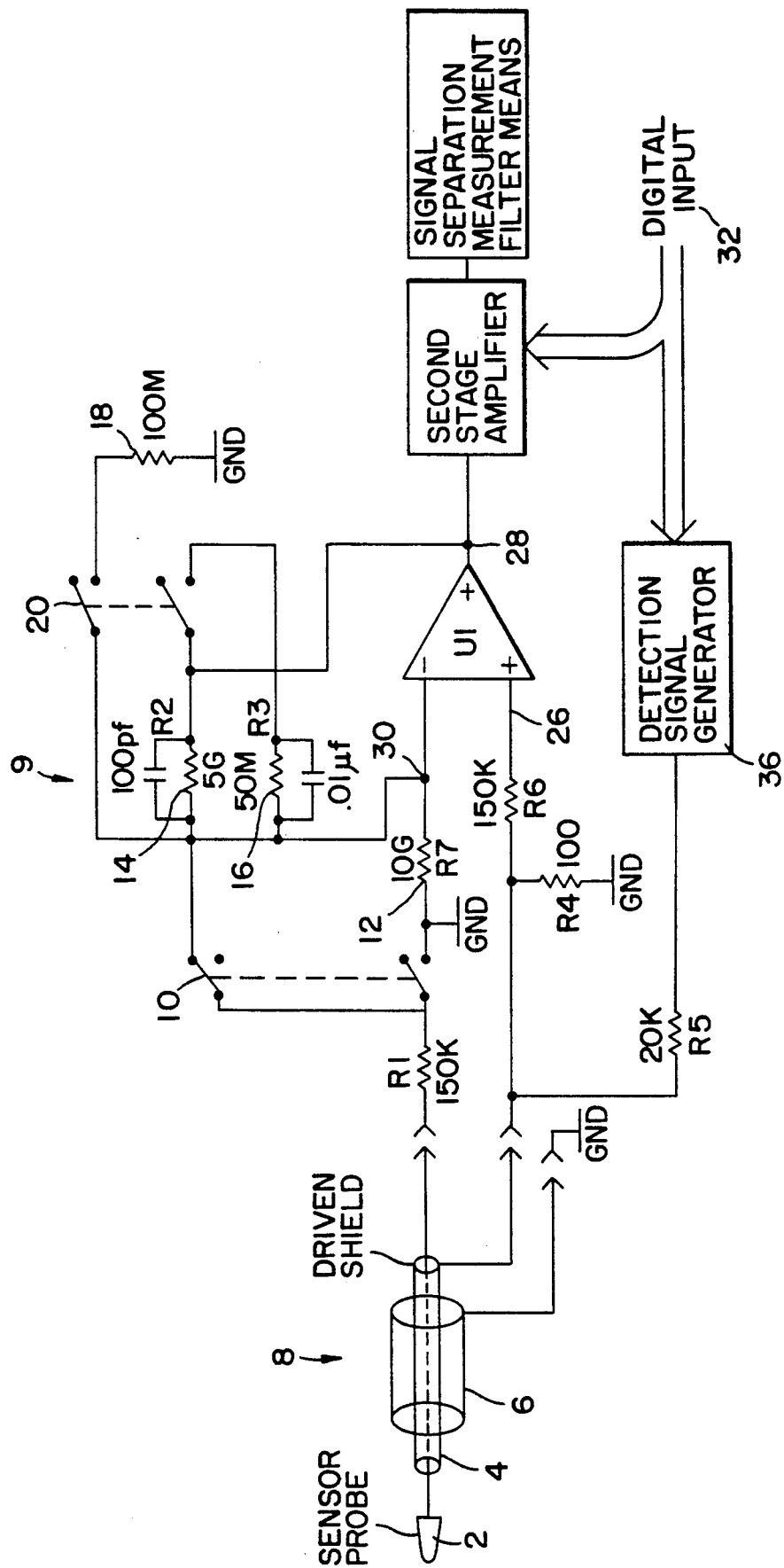

ON LINE TRIBOELECTRIC PROBE CONTAMINATION DETECTOR

CROSS REFERENCE TO RELATED APPLICATIONS

This application is closely related to U.S. Pat. Nos. 4,904,944 issued on Feb. 27, 1990; 4,714,890 issued on Dec. 22, 1987; 4,619,145 issued on Oct. 28, 1986; 4,774,453 issued on Sep. 27, 1988; 4,631,482 issued on Dec. 23, 1986. These patents are of common assignment with this application, and the disclosures of all are hereby incorporated by reference, as though set out at length herein.

FIELD OF THE INVENTION

The present invention relates to instrumentation for measurement of flow velocity and mass flow rates, and especially to electronic circuitry which connects directly to the physical measuring probe.

BACKGROUND OF THE INVENTION

The measurement of gas with solid particles therein and certain fluids which behave similarly, is of importance in many industries, e.g. chemical processing, food handling, transport loading and unloading, filtration, aeronautics and combustion fuel feeds. The above referenced patents have provided significant improvements in this general technical field.

Current flow measuring systems electrically connect the triboelectric sensor probe through an ultra low noise cable. The signal connection is fed to a core impedance conversion circuit (converter). A conversion circuit will amplify the input signal, where for the purposes of this invention amplification is defined broadly as voltage amplification, current amplification, impedance amplification (reduction) or combinations thereof. An over voltage protector is installed at the probe, and a current limiting barrier resistor before the converter's summing junction provides intrinsic safety for the probe and cable allowing the probe to be installed in hazardous environments.

Electrical offsets and drifts are of concern in the various circuits, and arrangements disclosed in the above referenced patents are used to compensate for these offsets and drifts. Other circuit implementations known in the art way also be used. Also various filters and other conditioning circuits, known in the art, may be used for noise elimination or other desired effects.

One of the continuing limitations of instrumentation, when practically applied in the above fields, to perform the measurement and feedback control of flow has been contamination of the physical probe. Any conductive substances, e.g. acids or other electrolytes, contained in the materials whose flow is being measured, may eventually build up providing electrical leakage paths which give rise to measurement errors. Also system errors occur as sensitivity (gain) and system zero change due to inexact temperature compensation, drift and/or other causes.

Old methods to solve this contamination problem have involved disassembly and cleaning or purging of the probe on a routine basis, and system calibration or other external testing circuits are used to monitor or measure system gain and zero. Employing these methods involves taking the system off-line and having skilled technicians perform the work.

It is an object of this invention to provide a circuit means which detects and quantifies, with the system on-line, when the probe is contaminated and needs cleaning.

It is another object of this invention to monitor and measure system gain and system zero while the system is on-line.

Another object of this invention is to minimize system down time and make efficient use of a technician's time.

It is an object of this invention that the probe-contamination, gain or zero change detection circuitry does not unduly interfere with or otherwise compromise the efficacy of the triboelectric detection instrumentation.

SUMMARY OF THE INVENTION

The present invention provides an improved circuit which allows the detection of contamination between the probe and ground, system gain changes and system zero changes without degrading or otherwise compromising the triboelectric instrument usefulness or sensitivity, and without unduly taking the system off-line.

An uncontaminated probe appears as an open circuit to the circuitry that receives the signal from the probe. The mass flow physically interacts with the probe creating a signal (triboelectric effect)—the signal being charge either supplied to the probe or taken from the probe. Compensation signals are fed into the receiving circuitry to counteract offsets and other drifts. In addition, a detection signal is fed into the converter and the resulting corresponding output signal from the converter is a measure of the voltage gain of the converter. If the voltage gain has not changed the probe is uncontaminated. Also, a circuit is implemented to allow determination that the system gain (independent of the probe contamination) and system zero are also acceptable.

In a preferred embodiment the probe is an open circuit, but when the probe is contaminated an electrical leakage path is established from the probe to the common signal return (ground). In this preferred embodiment the gain of the converter is dependent upon the impedance of the probe to the signal return. The detection signal experiences a gain due to the same circuit components as the probe signal experiences. When the probe impedance does not appear as an open circuit to the converter, the gain of the converter changes, and so a different level of the detection signal output is measured. This different level indicates a gain change which in turn indicates that the probe is contaminated and needs cleaning. The actual indicator to an operator may be of any known type including, but not limited to, a light, message display, flag or transmission.

The detection signal must be distinguished from a signal emanating from the triboelectric effect. Many techniques, known in the art may be used to accomplish this separation. In one preferred embodiment an alternating (AC) signal is used whereby the signal is easily extracted, by frequency filtering, or other means, in hardware or software, from the triboelectric signal without affecting the triboelectric signal. Hence there is no interaction between these signals and no degradation of the triboelectric instrument capabilities.

System zero is monitored by shunting the probe signal current directly to ground and disconnecting it from the converter input. With no signal the converter output may be measured to ensure that the system is at "zero". The switch may be an electronic or electromechanical relay, as in one preferred embodiment, a switch, any electronic switch (FET, transistor, etc) or the like.

Attaining the necessary system sensitivity requires the use of very high impedance components (resistors, op amps, etc) which sometimes malfunction. Switching means is used to isolate the probe and cable from the converter. The gain of the converter is then monitored to ensure acceptable gain. In addition, switch means may be used to select other resistors whereby the gain of the converter stage is checked including the high impedance resistors. Any fault is thereby related to the high impedance resistors or the other circuit components. These switch means are operated with the instrument on-line although the triboelectric measurement must be suspended for the short time of checking the system gain and zero.

Other objects, features, and advantages will be apparent from the following detailed description of preferred embodiments taken in conjunction with the accompanying drawing in which:

BRIEF DESCRIPTION OF THE DRAWINGS

FIG. 1 is a circuit/block diagram of a preferred embodiment of the present invention.

DETAILED DESCRIPTION OF PREFERRED EMBODIMENTS

FIG. 1 is a schematic/block diagram of a preferred embodiment of the present invention. In the on-line working configuration the latching relays K1 and K2 are activated as shown. R1 is connected to the inverting input 30 of an operational amplifier U1. Signal charge is transferred to the probe 2, defining a signal current (the time rate of charge transfer). This signal current is transformed into a voltage at the output of the op amp U1. U1 performs a current-to-voltage conversion (converter) of the signal current. In other embodiments a charge amplifier, a voltage amplifier, a current amplifier, an impedance transformer and combination thereof way be used. The converter input 30 is connected through resistor R7 to ground. Ground is herein defined as a signal return which way (but not necessarily) be 0 volts. The probe 2 is physically placed in the moving stream of material being measured, where charge per unit time (current) is transferred to the probe. That current is fed through the triaxial cable 8 to resistor R1. R1 is of a value which ensures that the probe can never exceed the current specification requirement for intrinsically safe circuitry as defined by Underwriters Laboratories, Factory Mutual Research, or other like safety organizations.

Current flows through R1 and enters the inverting summing junction 30 of op amp U1, with the latching relay K2 activated as shown. An equal current leaves the summing (inverting) junction via R2. R7 is very large (typically twice the value of R2), providing a specific voltage gain for the gain test signal and workable voltage at the output 28 of U1. U1 has low leakage or bias current and drift characteristics consistent with the signals being measured. The non-inverting input to U1, 26, is connected through R6 and R4 to ground, and compensation and detection signals are introduced to input 26 of U1 through R5, as discussed below.

The description of the typical operation of the circuit to measure signal current from the probe 2 follows. Small offsets, leakage currents and bias current are disregarded in the following discussion, but are routinely handled within the known art. Signal current runs through the triaxial cable 8 through R1 to the summing input 30 of U1. An equal current flows out from the summing junction through R2 due to the voltage output 28 of U1. Resistors R6 and R4 at the non-inverting input 26 of U1 are of a value that the voltage at 26 is at ground (discounting leakage and offsets). The operational amplifier U1 works to force the voltage at input 30 to be equal to the voltage at 26 and so input 30 is at ground and substantially no signal current flow through R7. The equivalent signal current flows through R2 creating a voltage drop across R2. This voltage drop is directly proportional to the signal current, and measurement of this voltage drop is a measure of the rate of charge picked up by the probe 2. Also, the integration of the voltage over time is a direct measure of the amount of charge picked up by the probe over the integration time.

Viewing the converter circuit from the input 26, with the relays activated as shown and the probe 2 an open circuit, the DC voltage gain from the input 26 to the output 28 is $1+(R2/R7)$. With a 5G ($G=1\times 10^9$) ohm R2 and a 10G ohm R7, this gain is 1.5. Introducing a known signal amplitude though R5 to input 26, and measuring the signal output at 28 the gain may be verified. If the gain is the expected 1.5 no service is indicated. But if the gain is not equal to 1.5 the probe may be contaminated, R7 and/or R2 may have drifted, or the op amp U1 and the supporting components may have malfunctioned. By activating K1 the probe signal is shunted to ground and is isolated from the converter circuitry, so that any contamination of the probe will not affect the gain of the converter. In this configuration if the gain is remeasured as 1.5, the probe is (most likely) contaminated and so requiring service. If the gain is not equal to 1.5, R2, R7 or U1 are most likely faulty. Activating K2 places much smaller resistors R3 and R8 in parallel with R2 and R7, respectively. In this preferred embodiment the ratio R3/R8 is the same as R7/R2—thus the same gain is maintained. Again by measuring the gain, the fault can be determined to be with the resistors R2 and/or R7 or with U1.

In this preferred embodiment the detection signal and the triboelectric signal are combined at the output of U1. The detection signal and the triboelectric signal must be separated from each other so neither interferes with the other. In this preferred embodiment the detection signal 36 is a frequency substantially entirely separated from the triboelectric signal by filter means 38, either in hardware or in software or a combination thereof. Other techniques of combining and separating ( multiplexing/demultiplexing) such signal together are well known in the art. In this embodiment the cable 8 may be long and contribute significant capacitance from the cable signal line to ground. The cable 8 is a triaxial cable wherein the inner shield 4 is driven from the same AC detection signal which appears on the cable signal line (from the input 30 through R1), causing the same voltage to appear on the signal conductor and inner shield, cancelling the capacitance effect of the cable. The range of frequencies for the detection signal may be broad only limited by the frequency effects of the circuitry and the ability to substantially completely separate the detection and triboelectric signals.

In a like manner the system zero is verified. With K1 shunting the probe signal to ground and isolating the converter input, and with no other inputs, the output of the op amp U1 should be at ground potential. If the output is not at ground then a drift or other malfunction occurred and service is indicated.

In practical applications the operation of the entire instrument will be verified as acceptable.

In summary, the verifications can be made without taking the instrument off-line, and if acceptable, no down time will be required. In addition faulty areas may be isolated from each other before taking the system off-line, and periodic checks of system zero and gain may be nude without taking the system off-line and with substantially no impact on the instrument's throughput.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. An improved triboelectric probe circuit comprising:
   (a) a converter means, wherein a triboelectric signal is received from the probe and converted to an amplified signal,
   (b) a triaxial cable connecting the probe to the converter, said triaxle cable containing a central conductor, an inner shield, an outer shield, and capacitance there between,
   (c) means for introducing an AC signal into said converter wherein said AC signal is converted to an amplified AC signal by utilizing essentially the same components as used to convert said triboelectric signal, and wherein said amplified triboelectric and AC signals are combined into an output signal, and wherein said amplification is dependent upon the probe being uncontaminated,
   (c) filter means for separating said amplified AC signal from the output signal, wherein said filter means comprises hardware, software, or combinations thereof.
   (d) means for measuring said amplified AC signal wherein a change in said amplified AC signal indicates a contaminated probe,
   (e) means for isolating said probe from said converter means, wherein a change in said AC signal output indicates a faulty circuit component,
   (f) means for grounding said triboelectric signal input to aid converter and isolating said converter inputs wherein said converter output acceptable system zero, and
   (g) means to drive said triaxial inner shield rendering said cable capacitance ineffective in distorting, or otherwise altering said output signal.

2. A triboelectric probe circuit comprising:
   (a) a converter means, with at least a first and a second input means and at least one output means, wherein a triboelectric signal is received at said first input means from a probe and converted to an amplified output signal,
   (b) means for introducing a detection signal into said converter via said second input means wherein said detection signal is converted to an amplified output detection signal by utilizing substantially the same components as used to convert said triboelectric signal, wherein said amplification is dependent upon the probe being uncontaminated, and
   (c) means for measuring said amplified output detection signal wherein a change in the value of said converted detection signal indicates a contaminated probe.

3. An improved circuit as defined in claim 2 further comprising means for isolating said probe from said converter means wherein the amplification of the converter means may be verified independent from said probe.

4. An improved circuit as defined in claim 2, wherein said triboelectric signal and said detection signal are converted and combined into an output signal, and further comprising means to separate said converted second signal from said output signal.

5. An improved circuit as defined in claim 2 further comprising means for grounding said first input means and isolating said converter inputs so that said converter output signal verifies an acceptable system zero.

6. An improved circuit as defined in claim 3 wherein said detection signal is an AC signal and said separating means comprises filter means for detecting and separating said AC signal from said triboelectric signal, and wherein said filter means comprises hardware, software or combinations thereof.

7. An improved circuit as defined in claim 5 further comprising shielded cable means, said shielded cable means defining, at least, signal conductor means, shield means and capacitance there between, connecting the probe to the converter means, and means to drive said shield rendering said cable capacitance ineffective in distorting or otherwise altering said output signal.

8. A triboelectric probe circuit comprising:
   (a) converter means, with at least a first and a second input means and at least one output means, wherein a triboelectric signal is received at said first input means from a probe and converted to an amplified output signal,
   (b) means for introducing a detection signal into said converter via said second input means wherein said detection signal is converted to an amplified output detection signal, wherein said amplification is dependent upon the probe being uncontaminated, and
   (c) means for measuring said amplified output detection signal wherein a change in the value of said converted detection signal indicates a contaminated probe.

9. An improved circuit as defined in claim 8 further comprising: means for isolating said probe from said converter means wherein the amplification of the converter means may be verified independent from said probe, and means for combining said triboelectric signal and detection signal into an output signal, and means to separate said converted detection signal from said output signal.

10. An improved circuit as defined in claim 9 further comprising means for grounding said inputs to said converter so that said converter output signal verifies an acceptable system zero.

11. An improved circuit as defined in claim 9 wherein said detection signal is an AC signal and said separating means comprises filter means for detecting and separating said AC signal from said triboelectric signal, and wherein said filter means comprises hardware, software or combinations thereof.

12. An improved circuit as defined in claim 11 further comprising shielded cable means, said shielded cable means defining, at least, signal conductor means, shield means and capacitance therebetween, connecting the probe to the converter means, and means to drive said shield rendering said cable capacitance ineffective in distorting or otherwise altering said output detection signal.

* * * * *